(12) United States Patent
O'Connor

(10) Patent No.: US 8,718,793 B2
(45) Date of Patent: May 6, 2014

(54) ELECTRODE INSERTION TOOLS, LEAD ASSEMBLIES, KITS AND METHODS FOR PLACEMENT OF CARDIAC DEVICE ELECTRODES

(75) Inventor: Stephen A. P. O'Connor, Bedfordshire (GB)

(73) Assignee: Cameron Health, Inc., San Clemente, CA (US)

( * ) Notice: Subject to any disclaimer, the term of this patent is extended or adjusted under 35 U.S.C. 154(b) by 1098 days.

(21) Appl. No.: 11/497,203

(22) Filed: Aug. 1, 2006

(65) Prior Publication Data

US 2008/0046056 A1    Feb. 21, 2008

(51) Int. Cl.
*A61N 1/05* (2006.01)

(52) U.S. Cl.
USPC .......................................................... 607/119

(58) Field of Classification Search
USPC .......................................... 607/119, 122, 129
See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |

(Continued)

FOREIGN PATENT DOCUMENTS

| | | |
|---|---|---|
| DE | 298 01 807 U1 | 7/1998 |
| EP | 0 095 727 A1 | 12/1983 |

(Continued)

OTHER PUBLICATIONS

Bardy, Gust H. et al., "Multicenter Experience with a Pectoral Unipolar Implantable Cardioverter-Defibrillator," *JACC*, Aug. 1996, vol. 28, No. 2, pp. 400-410.

(Continued)

*Primary Examiner* — Christopher D Koharski
*Assistant Examiner* — Michael D Abreu
(74) *Attorney, Agent, or Firm* — Schwegman, Lundberg & Woessner, P.A.

(57) ABSTRACT

Insertion tools, lead assemblies, kits, and methods for placement of cardiac device electrodes. In some embodiments, an insertion tool having a proximal end and a distal, dissecting end includes a structure configured to receive or engage a structure on a lead assembly. Some embodiments include a lead assembly having an end including a structure configured for engaging the distal end of an associated insertion tool. Some embodiments include kits or systems including both an insertion tool and a lead assembly, each having a structure for engaging the other. In these embodiments, the engaging structures may take several forms including threads, small posts, circular or semi-circular receiving members, and/or a slot. Some embodiments also include methods for placement of cardiac device electrodes with the assistance of an associated insertion tool, wherein the cardiac device electrodes are associated with a lead assembly having an end configured to engage a distal, dissecting portion of an associated insertion tool.

9 Claims, 16 Drawing Sheets

(56) References Cited

U.S. PATENT DOCUMENTS

| | | | |
|---|---|---|---|
| 4,270,549 A | 6/1981 | Heilman | |
| 4,291,707 A | 9/1981 | Heilman et al. | |
| 4,300,567 A | 11/1981 | Kolenik et al. | |
| 4,314,095 A | 2/1982 | Moore et al. | |
| 4,375,817 A | 3/1983 | Engle et al. | |
| 4,402,322 A | 9/1983 | Duggan | |
| 4,407,288 A | 10/1983 | Langer et al. | |
| 4,424,818 A | 1/1984 | Doring et al. | |
| 4,450,527 A | 5/1984 | Sramek | |
| 4,471,777 A * | 9/1984 | McCorkle, Jr. | 606/129 |
| 4,548,209 A | 10/1985 | Weilders et al. | |
| 4,567,900 A | 2/1986 | Moore | |
| 4,595,009 A | 6/1986 | Leinders | |
| 4,596,559 A | 6/1986 | Fleischhacker | |
| 4,602,637 A | 7/1986 | Elmqvist et al. | |
| 4,603,705 A | 8/1986 | Speicher et al. | |
| 4,693,253 A | 9/1987 | Adams | |
| 4,727,877 A | 3/1988 | Kallok | |
| 4,750,494 A | 6/1988 | King | |
| 4,765,341 A | 8/1988 | Mower et al. | |
| 4,768,512 A | 9/1988 | Imran | |
| 4,800,883 A | 1/1989 | Winstrom | |
| 4,830,005 A | 5/1989 | Woskow | |
| 4,944,300 A | 7/1990 | Saksena | |
| 5,011,482 A * | 4/1991 | Goode et al. | 606/1 |
| 5,044,374 A | 9/1991 | Lindemans et al. | |
| 5,105,810 A | 4/1992 | Collins et al. | |
| 5,105,826 A | 4/1992 | Smits et al. | |
| 5,109,842 A | 5/1992 | Adinolfi | |
| 5,129,392 A | 7/1992 | Bardy et al. | |
| 5,133,353 A | 7/1992 | Hauser | |
| 5,144,946 A | 9/1992 | Weinberg et al. | |
| 5,184,616 A | 2/1993 | Weiss | |
| 5,191,901 A | 3/1993 | Dahl et al. | |
| 5,203,348 A | 4/1993 | Dahl et al. | |
| 5,215,081 A | 6/1993 | Ostroff | |
| 5,230,337 A | 7/1993 | Dahl et al. | |
| 5,255,692 A | 10/1993 | Neubauer et al. | |
| 5,261,400 A | 11/1993 | Bardy | |
| 5,300,106 A | 4/1994 | Dahl et al. | |
| 5,313,953 A | 5/1994 | Yomtov et al. | |
| 5,331,966 A | 7/1994 | Bennett et al. | |
| 5,342,407 A | 8/1994 | Dahl et al. | |
| 5,366,496 A | 11/1994 | Dahl et al. | |
| 5,376,103 A | 12/1994 | Anderson et al. | |
| 5,376,104 A | 12/1994 | Sakai et al. | |
| 5,385,574 A | 1/1995 | Hauser et al. | |
| 5,391,200 A | 2/1995 | KenKnight et al. | |
| 5,405,363 A | 4/1995 | Kroll et al. | |
| 5,411,539 A | 5/1995 | Neisz | |
| 5,411,547 A | 5/1995 | Causey, III | |
| 5,413,591 A | 5/1995 | Knoll | |
| 5,423,326 A | 6/1995 | Wang et al. | |
| 5,439,485 A | 8/1995 | Mar et al. | |
| 5,447,521 A | 9/1995 | Anderson et al. | |
| 5,476,503 A | 12/1995 | Yang | |
| 5,509,923 A | 4/1996 | Middleman et al. | |
| 5,509,928 A | 4/1996 | Acken | |
| 5,531,765 A | 7/1996 | Pless | |
| 5,531,766 A | 7/1996 | Kroll et al. | |
| 5,534,019 A | 7/1996 | Paspa | |
| 5,534,022 A | 7/1996 | Hoffmann et al. | |
| 5,597,956 A | 1/1997 | Ito et al. | |
| 5,601,607 A | 2/1997 | Adams | |
| 5,603,732 A | 2/1997 | Dahl et al. | |
| 5,607,455 A | 3/1997 | Armstrong | |
| 5,618,287 A | 4/1997 | Fogarty et al. | |
| 5,620,477 A | 4/1997 | Pless et al. | |
| 5,643,328 A | 7/1997 | Cooke et al. | |
| 5,645,586 A | 7/1997 | Meltzer | |
| 5,658,317 A | 8/1997 | Haefner et al. | |
| 5,658,319 A | 8/1997 | Kroll | |
| 5,658,321 A | 8/1997 | Fayram et al. | |
| 5,665,093 A | 9/1997 | Atkins et al. | |
| 5,674,260 A | 10/1997 | Weinberg | |
| 5,683,447 A | 11/1997 | Bush et al. | |
| 5,690,648 A | 11/1997 | Fogarty et al. | |
| 5,690,683 A | 11/1997 | Haefner et al. | |
| 5,693,081 A | 12/1997 | Fain et al. | |
| 5,697,953 A | 12/1997 | Kroll et al. | |
| 5,713,926 A | 2/1998 | Hauser et al. | |
| 5,766,226 A | 6/1998 | Pedersen | |
| 5,776,169 A | 7/1998 | Schroeppel | |
| 5,782,841 A | 7/1998 | Ritz et al. | |
| 5,814,090 A | 9/1998 | Latterell et al. | |
| 5,827,326 A | 10/1998 | Kroll et al. | |
| 5,836,976 A | 11/1998 | Min et al. | |
| 5,843,132 A | 12/1998 | Ilvento | |
| 5,895,414 A | 4/1999 | Sanchez-Zambrano | |
| 5,902,331 A * | 5/1999 | Bonner et al. | 607/122 |
| 5,904,705 A | 5/1999 | Kroll et al. | |
| 5,919,211 A | 7/1999 | Adams | |
| 5,919,222 A | 7/1999 | Hjelle et al. | |
| 5,925,069 A | 7/1999 | Graves et al. | |
| 5,935,154 A | 8/1999 | Westlund | |
| 5,941,904 A | 8/1999 | Johnston et al. | |
| 5,957,956 A | 9/1999 | Kroll et al. | |
| 6,014,586 A | 1/2000 | Weinberg et al. | |
| 6,026,325 A | 2/2000 | Weinberg et al. | |
| 6,058,328 A | 5/2000 | Levine et al. | |
| 6,093,173 A | 7/2000 | Balceta et al. | |
| 6,095,987 A | 8/2000 | Shmulewitz et al. | |
| H1905 H | 10/2000 | Hill | |
| 6,128,531 A | 10/2000 | Campbell-Smith | |
| 6,144,866 A | 11/2000 | Miesel et al. | |
| 6,144,879 A | 11/2000 | Gray | |
| 6,148,230 A | 11/2000 | KenKnight | |
| 6,183,485 B1 | 2/2001 | Thomason et al. | |
| 6,185,450 B1 | 2/2001 | Seguine et al. | |
| 6,215,231 B1 | 4/2001 | Newnham et al. | |
| 6,266,567 B1 | 7/2001 | Ishikawa et al. | |
| 6,278,894 B1 | 8/2001 | Salo et al. | |
| 6,280,462 B1 | 8/2001 | Hauser et al. | |
| 6,324,414 B1 * | 11/2001 | Gibbons et al. | 600/373 |
| 6,327,492 B1 | 12/2001 | Lemelson | |
| 6,332,089 B1 | 12/2001 | Acker et al. | |
| 6,334,071 B1 | 12/2001 | Lu | |
| 6,345,198 B1 | 2/2002 | Mouchawar et al. | |
| 6,348,045 B1 | 2/2002 | Malonek et al. | |
| 6,360,130 B1 | 3/2002 | Duysens et al. | |
| 6,411,844 B1 | 6/2002 | Kroll et al. | |
| 6,605,094 B1 * | 8/2003 | Mann et al. | 606/129 |
| 6,647,292 B1 | 11/2003 | Bardy et al. | |
| 6,721,597 B1 | 4/2004 | Bardy et al. | |
| 6,752,827 B2 | 6/2004 | Ross et al. | |
| 6,754,528 B2 | 6/2004 | Bardy et al. | |
| 6,778,860 B2 | 8/2004 | Ostroff et al. | |
| 6,788,974 B2 | 9/2004 | Bardy et al. | |
| 6,834,204 B2 | 12/2004 | Ostroff et al. | |
| 6,856,835 B2 | 2/2005 | Bardy et al. | |
| 6,865,417 B2 | 3/2005 | Rissmann et al. | |
| 6,866,044 B2 | 3/2005 | Bardy et al. | |
| 6,927,721 B2 | 8/2005 | Ostroff et al. | |
| 6,937,907 B2 | 8/2005 | Bardy et al. | |
| 6,950,705 B2 | 9/2005 | Bardy et al. | |
| 6,952,608 B2 | 10/2005 | Ostroff | |
| 6,952,610 B2 | 10/2005 | Ostroff et al. | |
| 6,954,670 B2 | 10/2005 | Ostroff | |
| 6,988,003 B2 | 1/2006 | Bardy et al. | |
| 7,020,523 B1 | 3/2006 | Lu et al. | |
| 7,027,858 B2 | 4/2006 | Cao et al. | |
| 7,039,459 B2 | 5/2006 | Bardy et al. | |
| 7,039,463 B2 | 5/2006 | Marcovecchio | |
| 7,062,329 B2 | 6/2006 | Ostroff et al. | |
| 7,065,407 B2 | 6/2006 | Bardy et al. | |
| 7,065,410 B2 | 6/2006 | Bardy et al. | |
| 7,069,080 B2 | 6/2006 | Bardy et al. | |
| 7,076,294 B2 | 7/2006 | Bardy et al. | |
| 7,076,296 B2 | 7/2006 | Rissmann et al. | |
| 7,090,682 B2 | 8/2006 | Sanders et al. | |
| 7,092,754 B2 | 8/2006 | Bardy et al. | |
| 2001/0027330 A1 | 10/2001 | Sullivan et al. | |
| 2002/0103424 A1 * | 8/2002 | Swoyer et al. | 600/350 |
| 2002/0188252 A1 | 12/2002 | Bardy | |

(56) References Cited

U.S. PATENT DOCUMENTS

| | | |
|---|---|---|
| 2004/0254611 A1 | 12/2004 | Palreddy et al. |
| 2004/0254613 A1 | 12/2004 | Ostroff et al. |
| 2004/0260370 A1 | 12/2004 | Ley et al. |
| 2005/0049644 A1 | 3/2005 | Warren et al. |
| 2006/0079796 A1 | 4/2006 | Marcovecchio et al. |
| 2006/0085038 A1 | 4/2006 | Linder et al. |

FOREIGN PATENT DOCUMENTS

| | | |
|---|---|---|
| EP | 0 316 616 A2 | 5/1989 |
| EP | 0 316 616 A3 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | WO 02/068046 A1 | 9/2002 |
| WO | WO 03/018121 A2 | 3/2003 |
| WO | WO 03/022352 A1 | 3/2003 |
| WO | WO 03/039666 A1 | 5/2003 |

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361-362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Higgins, Steven L. et al., "The First Year Experience with the Dual Chamber ICD," *PACE*, Jan. 2000, vol. 23, pp. 18-25.

Mirowski, M. et al., "Automatic Detection and Defibrillation of Lethal Arrhythmias—A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," *IEEE*, (1987) pp. 167-170.

Schuder, John C., "Completely Implanted Defibrillator," *JAMA*, vol. 214, No. 6, Nov. 9, 1970. p. 1123 (single sheet).

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Schwacke, H. et al., "Komplikationen mit Sonden bei 340 Patienten mit einem Implantierbaren Kardioverter/Defibrillator," *Z Kardiol* (1999)vol. 88, No. 8, pp. 559-565.

Throne, Robert D. et al., "A Comparison of Four New Time-Domain Techniques for Discriminating Monomorphic Ventricular Tachycardia from Sinus Rhythm Using Ventricular Waveform Morphology," *IEEE Transactions on Biomedical Engineering*, vol. 38, No. 6, Jun. 1991, pp. 561-570.

Tietze U. et al., "Halbleiter-Schaltungstechnik," © Springer-Verlag (Berlin, Germany), (1991), pp. 784-786.

Valenzuela, Terrence D. et al., "Outcomes of Rapid Defibrillation by Security Officers After Cardiac Arrest in Casinos," *The New England Journal of Medicine*, Oct. 26, 2000, vol. 343, No. 17, pp. 1206-1209.

Walters, R.A. et al., "Analog to Digital Conversion Techniques in Implatable Devices," *Annual International Conference of the IEEE Engineering in Medicine and Biology Society*, vol. 13 No. 4 (1991) p. 1674-1676.

\* cited by examiner

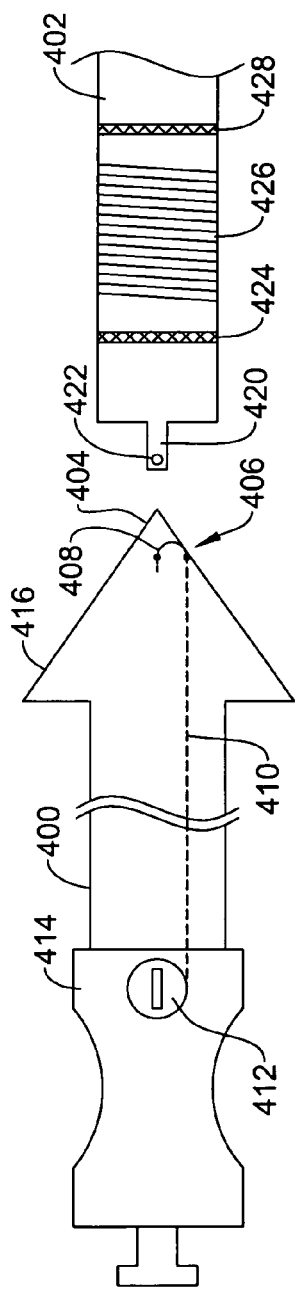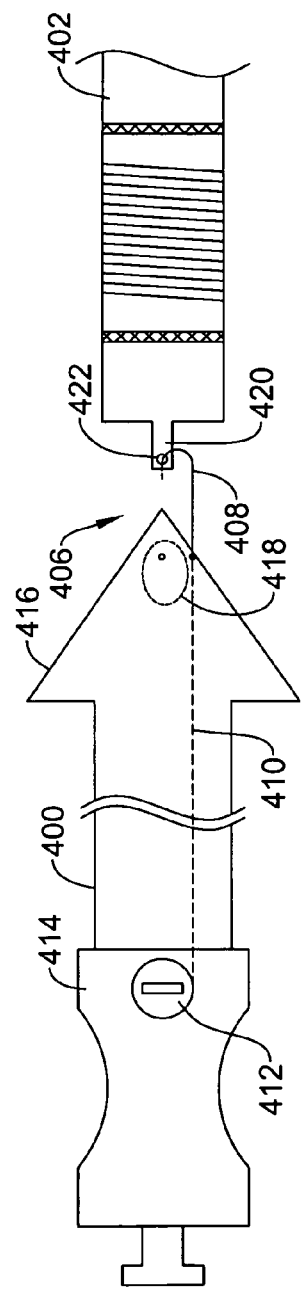
Figure 6A
Figure 6B

ELECTRODE INSERTION TOOLS, LEAD ASSEMBLIES, KITS AND METHODS FOR PLACEMENT OF CARDIAC DEVICE ELECTRODES

CROSS REFERENCE TO RELATED APPLICATIONS

The present application is related to that of U.S. patent application Ser. No. 11/006,291, titled APPARATUS AND METHOD FOR SUBCUTANEOUS ELECTRODE INSERTION, published as US 2006-0122676 A1 on Jun. 8, 2006 and now U.S. Pat. No. 7,655,014, which is incorporated herein by reference.

FIELD

The present invention relates to the field of implantable cardiac stimulus device systems. More specifically, the present invention relates to insertion tools, lead assemblies, methods and kits for placement of cardiac device electrodes.

BACKGROUND

Implantable cardiac stimulus and/or monitoring devices and systems are known for use in ongoing and prophylactic treatment of cardiac conditions as well as diagnosis of cardiac maladies. Often such systems will include one or more lead assemblies that carry electrodes that may be used to sense cardiac activity and/or to deliver therapy to the patient. Convenient and uncomplicated, as well as quick, implantation of the lead assemblies is desirable, and alternatives to existing technologies and methods are sought.

SUMMARY

The present invention is, in several embodiments, directed toward insertion tools, lead assemblies, kits, and methods for placement of cardiac device electrodes. In some embodiments, an insertion tool having a proximal end and a distal, dissecting end includes a structure configured to receive or engage a structure on a lead assembly. Some embodiments include a lead assembly having an end including a structure configured for engaging the distal end of an associated insertion tool. Some embodiments include kits or systems including both an insertion tool and a lead assembly, each having a structure for engaging the other. In these embodiments, the engaging structures may take several forms including threads, small posts, circular or semi-circular receiving members, and/or a slot. Some embodiments also include methods for placement of cardiac device electrodes with the assistance of an associated insertion tool, wherein the cardiac device electrodes are associated with a lead assembly having an end configured to engage a distal, dissecting portion of an associated insertion tool.

BRIEF DESCRIPTION OF THE DRAWINGS

FIGS. 6A and 6B are side views of an illustrative electrode insertion tool and an illustrative lead in detached and attached configurations;

DETAILED DESCRIPTION

The following detailed description should be read with reference to the drawings. The drawings, which are not necessarily to scale, depict illustrative embodiments and are not intended to limit the scope of the invention.

As used herein, the proximal end of an electrode insertion tool is the end having a handle for grasping by the physician, and the distal end of an electrode insertion tool is the end having a dissecting tip for forming a path or opening through tissue and/or between layers of tissue. The proximal end of a lead electrode assembly is the end that is connected to an associated canister, while other end of a lead electrode assembly is referred to as the distal end.

Figure 1:
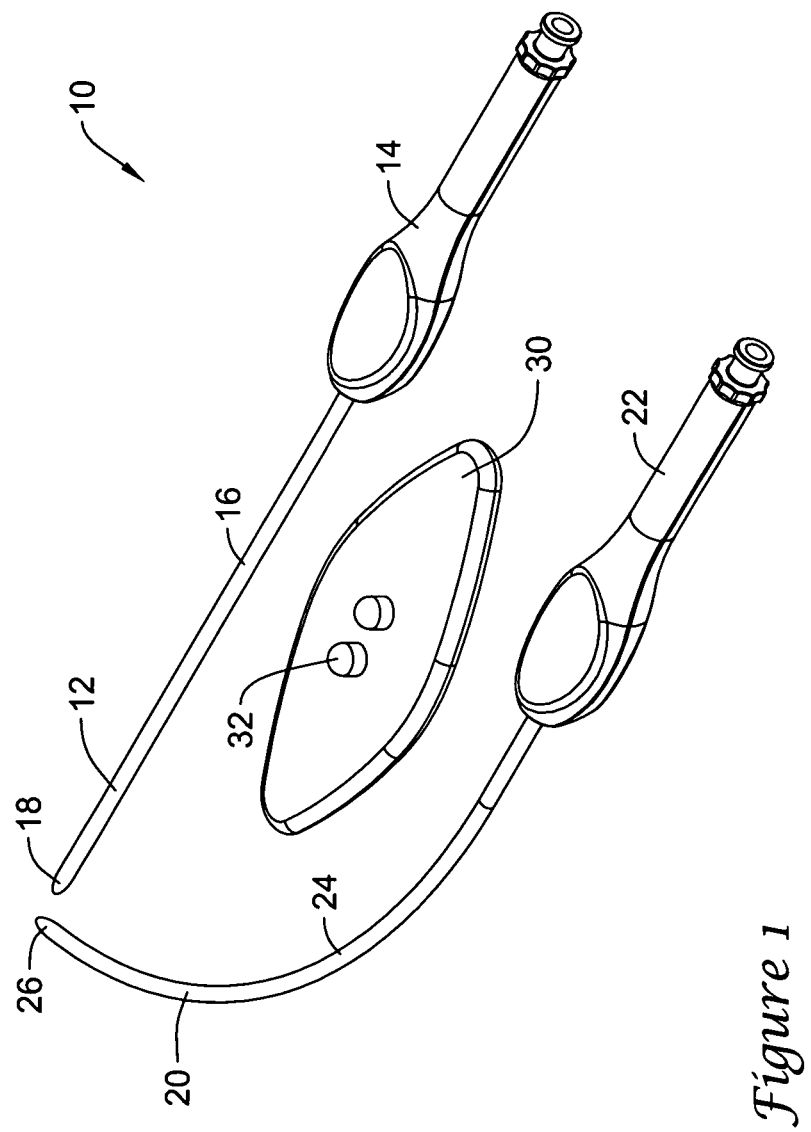
FIG. 1 is a perspective view of an illustrative electrode insertion tool set.

FIG. 1 is a perspective view of an illustrative electrode insertion tool set. The illustrative set 10 includes several elements, including a straight introducer 12 having a handle 14, a shaft 16, and a distal tip 18. A curved introducer 20 is also shown, and includes a handle 22, a shaft 24, and a distal tip 26. A shaping tool 30 is also shown, the shaping tool having posts 32 disposed thereon. The shaping tool 30 may be used to adjust the curvature or shape of either of the introducers 12, 20. The handle of either or both introducers 12, 20 may include a port for fluid infusion, and the shafts 16, 24 or distal tips 18, 26 may include one or more ports allowing fluid (such as a local anesthetic, for example, lidocaine) to be infused during the insertion procedure. The distal tips 18, 26 may be shaped for blunt dissection including, for example, a relatively sharp distal tip portion forming a generally conical dissection element. This allows for piercing and/or separation of tissue to form a space for insertion of a lead electrode assembly.

In an illustrative embodiment, a straight electrode insertion tool has an overall length, including the handle, of about 26.5 cm, with the shaft having an outer diameter of about 3.2 millimeters. Other embodiments may range from about 1 mm to about 6 mm in outer shaft diameter, with an overall length between about 10 cm and about 40 cm. An illustrative shaft is formed of stainless steel, with a polycarbonate proximal handle. Alternatively, a polymer providing added shapeability may be used for the shaft. A polytetrafluoroethylene coating may be used, if desired. Other coatings may be used, including drug eluting coatings. The overall size may be modified in light of patient anatomy, desired implant location, and the size of the lead electrode assembly being used, for example.

FIGS. 2A-2E show steps of an illustrative method of implantation of a cardiac stimulus device and lead assembly to a subcutaneous location. Beginning with FIG. 2A, a patient 40 is shown having a heart generally at 42, with the median or sagittal plane shown generally at 44. At a location about 0 cm to about 4 cm superior or inferior to the xiphoid process 46, a first incision 48 is made at a medial location. In an illustrative embodiment, the first incision 48 is about 1 cm to about 2 cm inferior to the xiphoid process. A subcutaneous pocket 50 may be formed in a suitable fashion for receiving the canister of the cardiac stimulus device, with the subcutaneous pocket 50 formed near a second incision 52. An electrode insertion tool is shown, with shaft 54 and handle 56, and, as indicated by the arrow, is inserted through the first incision 48 and advanced toward the second incision 52, creating a channel through the patient's subcutaneous tissue.

Figure 2A:
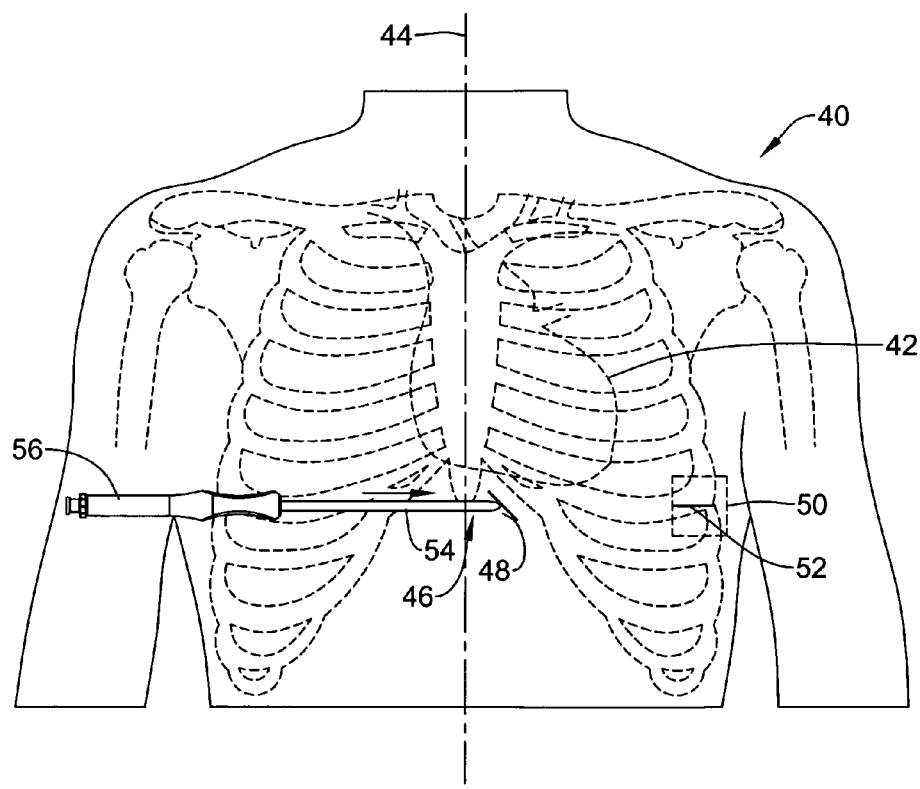
FIGS. 2A-2E show steps of an illustrative method of implantation of a cardiac stimulus device.
Figure 2B:
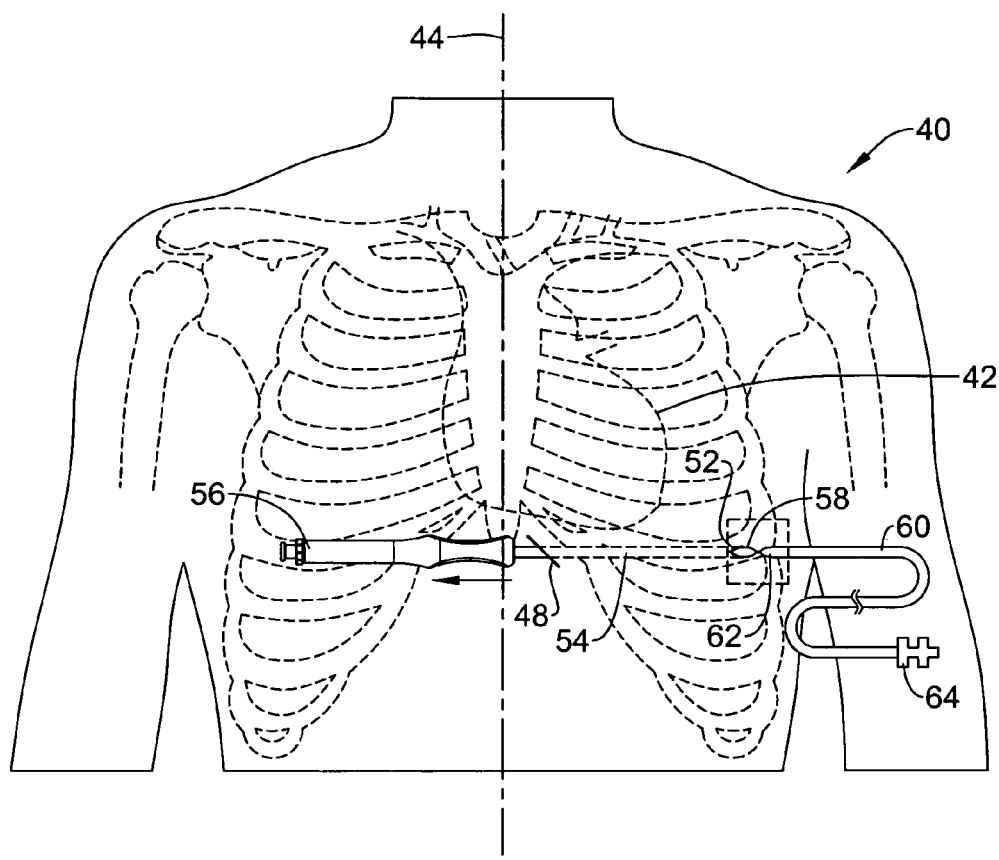

Turning to FIG. 2B, the insertion tool is advanced through first incision 48 toward the second incision 52 through subcutaneous tissue until the distal end 58 exits the second incision 52, such that the shaft 54 temporarily resides in the subcutaneous tissue of the patient. Next, a lead assembly 60 is provided, with a distal end 62 and a proximal end 64. The proximal end of the lead assembly 60 is shown including a plug or connector for attachment to an associated canister. The distal end 62 of the lead assembly 60 is secured to the distal end 58 of the electrode insertion tool. The physician then grasps the handle 56 and, as indicated by the arrow, withdraws the electrode insertion tool via the first incision 48, pulling the lead assembly 60 into the subcutaneous space or channel previously dissected.

Figure 2C:
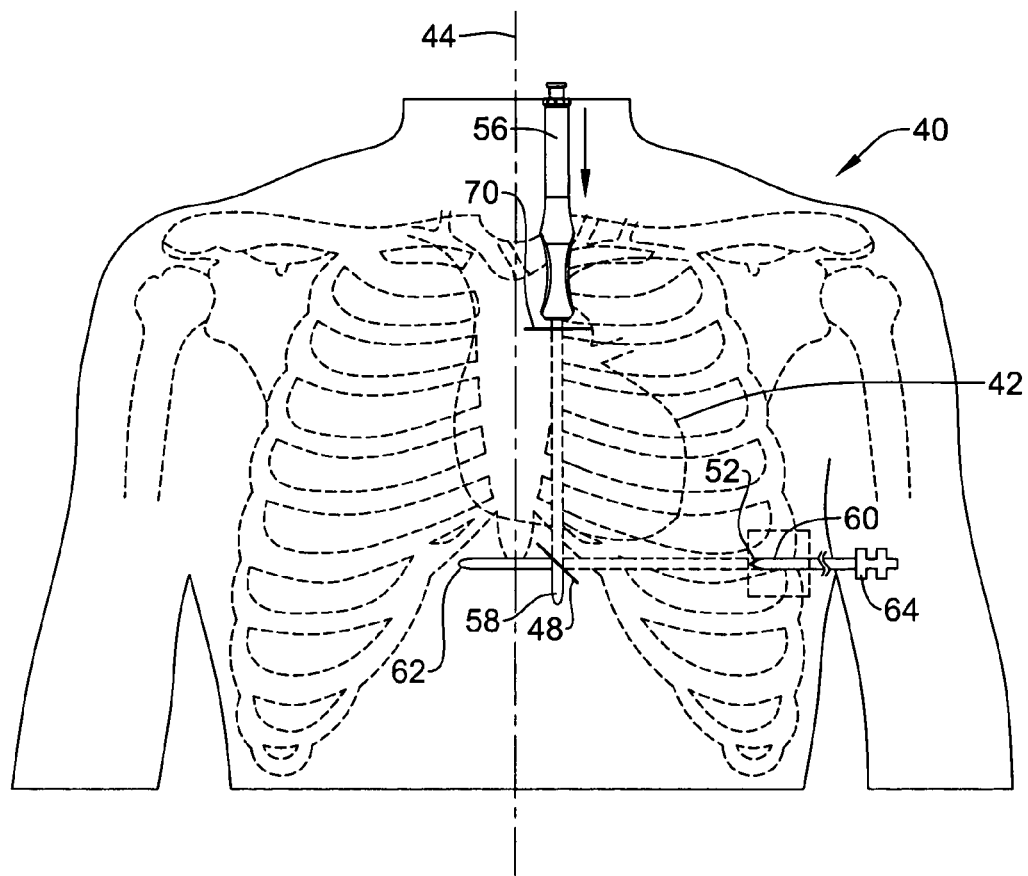

Referring now to FIG. 2C, the result of the steps shown in FIG. 2B is that the lead assembly 60 now resides partly in the patient's subcutaneous tissue, with the proximal end with plug or connector 64 sitting outside of the patient near the second incision 52, and the distal end 62 extending out of first incision 48. As indicated in FIG. 2C, the next step is for the insertion tool to be inserted through a third incision 70 and advanced toward and through the first incision 48. The third incision 70 may be approximately 8-10 cm (or more or less, depending on patient anatomy) above the first incision 48, to the left of the median or sagittal plane 44, and cephalad of the first incision 48. The first and second incisions may be placed such that a line drawn therebetween is parallel to the patient's sternal midline, with the incisions being spaced about 0 cm to about 5 cm to the left of the sternal midline. In the embodiment shown, a parasternal implant location is achieved by placing the incisions about 3 cm to the left of the sternal midline. The insertion tool is advanced toward the first incision 48 until the distal end 58 of the insertion tool exits the first incision 48.

Figure 2D:
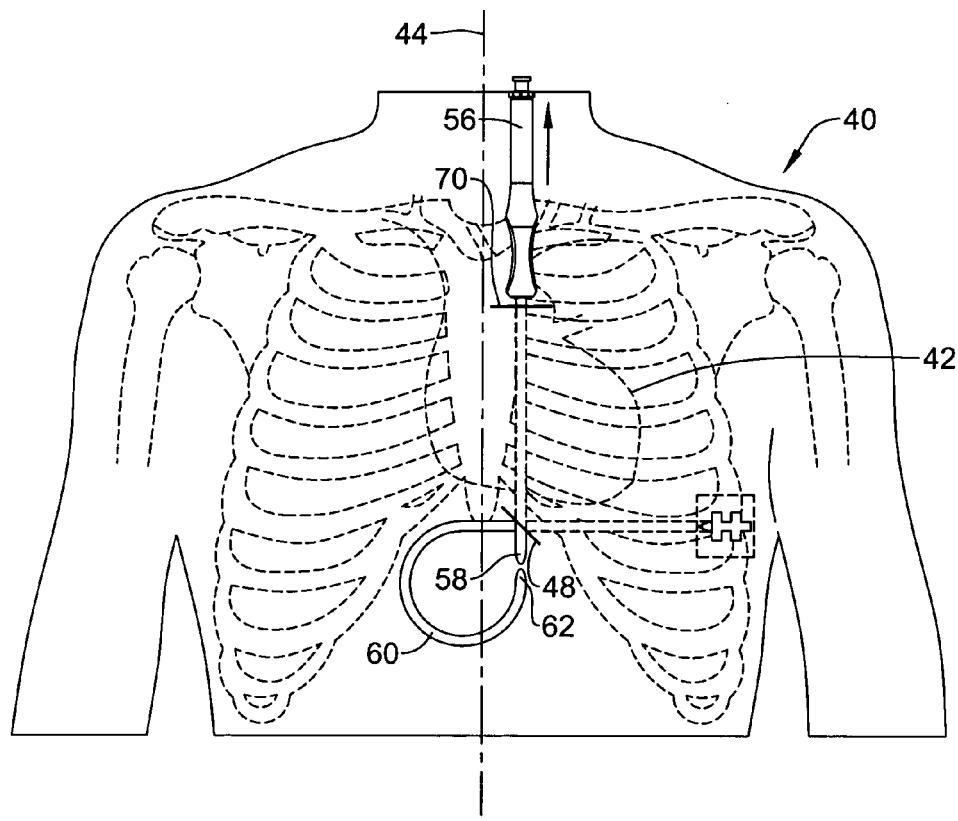

Turning to FIG. 2D, the lead assembly 60 is manipulated such that its distal end 62 is adjacent the distal end 58 of the insertion tool. The distal end 62 of the lead assembly 60 is then secured to the distal end 58 of the insertion tool. An implanting physician then grasps the handle 56 and withdraws the insertion tool as indicated by the arrow, pulling the distal end 62 of the lead assembly 60 toward the third incision 70.

Figure 2E:
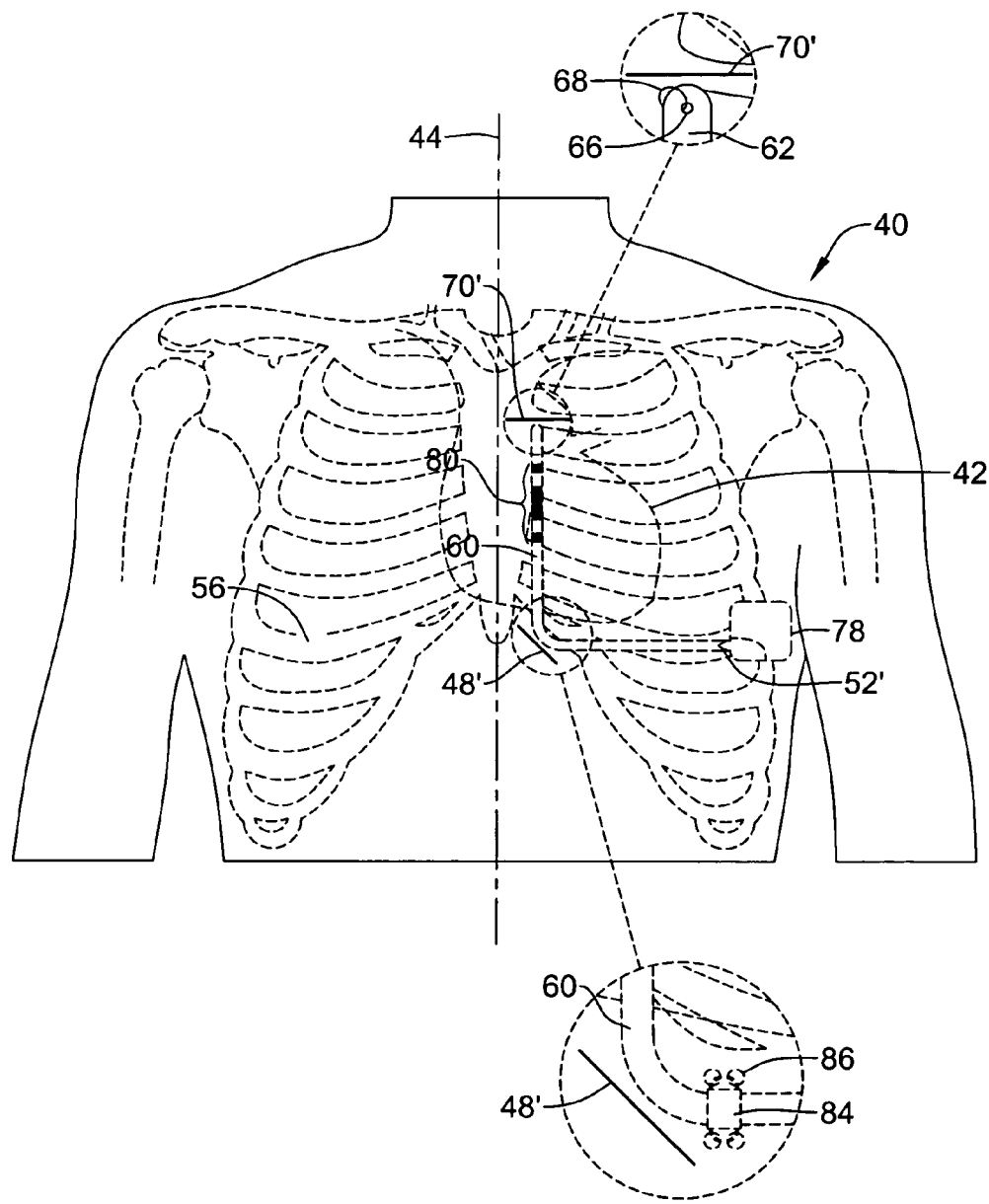

FIG. 2E illustrates the completed procedure. The lead assembly 60 is disposed in a subcutaneous space in a generally "L" shape. The distal end 62 of the lead assembly 60 is disposed near the third incision, which is shown as a closed incision 70'. As shown by the insets, the distal end 62 of the lead assembly 60 may be secured, using suture hole 66, to the fascia near the third incision by sutures 68. Likewise, a medial portion of the lead assembly 60 may be secured to fascia near the first incision (shown as closed incision 48') using suture(s) 86 that are secured to a suture sleeve 84 that may be secured to the lead assembly 60. The addition of these sutures 68, 86 is optional, but may aid in acute retention of the position of implantation. As time passes, tissue surrounding the electrode and/or lead assembly will fibrose and also hold the lead assembly in place. For example, the sutures 68, 86 may formed of biocompatible, dissolvable material.

FIG. 2E also illustrates placement of the canister 78 relative to the rest of the implanted system. In particular, the canister 78 is placed near the second incision (shown at closed incision 52') in the subcutaneous pocket 50 (FIG. 2A). The lead assembly 60 is secured to the canister 78, and extends first medially toward the first incision (shown as closed incision 48') and then cephalad toward the third incision (shown at closed incision 70').

A distal portion of the lead assembly 60 is shown as including a plurality of electrodes, as shown at 80. The number and type of electrode(s) may vary, with at least one electrode included. In an illustrative embodiment, the electrodes 80 include a distal ring electrode used primarily for sensing, a proximal ring electrode also used primarily for sensing, and a coil electrode therebetween, with the coil electrode used for delivering stimulus, although each electrode may perform more than one function. The canister 78 may also include one or more electrodes. The lead assembly 60 further includes a proximally extending shaft having conductors passing therethrough, with the shaft providing insulation to the conductors, and with the conductor(s) coupled to the one or more electrodes.

Alternatives to the steps shown in FIGS. 2A-2E are available in other embodiments. In some embodiments, the first incision 48 and/or third incision 70 may be at different locations, for example, to the right of the median or saggital plane, or, rather than at an anterior position as shown, posterior to the patient. Further, the pocket 50 for receiving the canister of the system may be moved to a more cephalad position (for example, near the clavicle). The canister 78 is shown as generally rectangular, although other shapes, including a long, narrow shape that conforms to the patient's ribcage, may instead be used.

Part of the implantation procedure shown in FIGS. 2A-2E includes steps in which an electrode insertion tool is used to first create a subcutaneous pathway, is then connected at its distal end to a lead assembly, and is then used to pull the lead assembly through the just created subcutaneous pathway. When the desired configuration has an "L" shape as shown by FIG. 2E, these steps may be performed twice, such that either one electrode insertion tool is coupled to, de-coupled from, re-coupled to, and re-de-coupled from the lead assembly, or first and second electrode insertion tools are successively coupled to and decoupled from the lead assembly. In either event, it is desired to have the ability to readily and easily couple the lead assembly to the electrode insertion tool to perform the step of pulling the lead assembly through the patient's subcutaneous tissue to a desired location. Following are several illustrative examples that provide such functionality.

It may also be noted that the implantation procedure in FIGS. 2A-2E does not require the use of a splittable sheath. Additional structures, such as a sheath or a splittable sheath may be added, if desired, but the procedure does not require such elements. The method thus includes establishing a subcutaneous pathway by the use of an implantation tool, securing a lead assembly for use in the cardiac device system to the implantation tool, and pulling the lead assembly into the subcutaneous pathway, wherein the lead assembly is pulled into the subcutaneous pathway in its finished condition, without the use of a sheath or splittable sheath thereon.

Figure 3A:
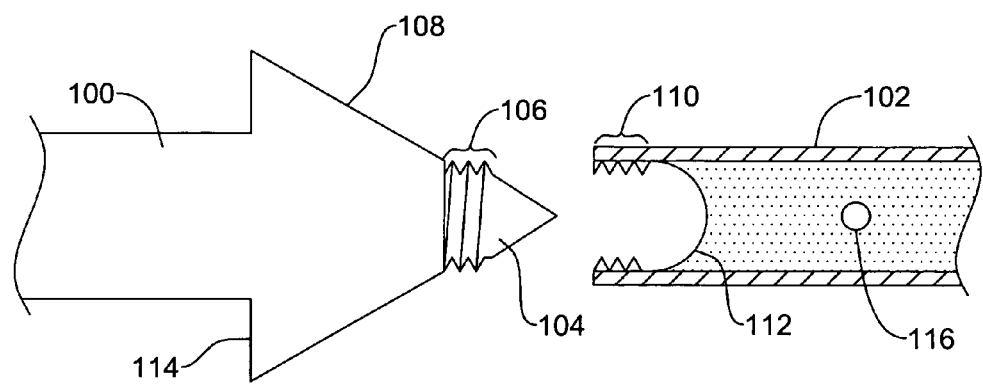
FIGS. 3A and 3B are side views of an illustrative electrode insertion tool and an illustrative lead in detached and attached configurations.

FIG. 3A is a side view of an illustrative electrode insertion tool 100 and an illustrative lead assembly 102 in a detached configuration. FIG. 3A generally shows the distal ends of each of the illustrative electrode insertion tool 100 and the illustrative lead assembly 102. The electrode insertion tool 100 includes a dissecting tip 104, which is shown as a generally sharp member. Proximal and adjacent to the dissecting tip 104 is a lead engaging structure 106 that is configured for engaging the lead assembly 102. Further proximal on the electrode insertion tool 100 is a dissecting portion 108 that is shaped to further expand and dissect subcutaneous space as the electrode insertion tool 100 is advanced through subcutaneous tissue.

The lead assembly 102 also includes an engagement structure 110 that is configured to engage and secure to the tool 100. In the illustrative embodiment, the engagement structures 106, 110 take the form of cooperating threading that allows for rotational fixation of the lead assembly 102 to the introducer 100. The lead assembly 102 defines, at its distal end, a cavity wall 112 shaped to receive the dissecting tip 104 therein. As such, the lead assembly 102 includes a receiving structure including both the engagement structure 110 and the cavity/cavity wall 112. Also shown on the lead assembly 102 is a suture hole 116, which may be used, as illustrated in FIG. 2E, to provide an acute or chronic retention structure.

The electrode insertion tool 100 is shown as including a proximally facing shoulder 114. This shoulder 114 may be abrupt, as shown, or may be smoothed or curved in to avoid catching on and/or tearing subcutaneous tissue as the electrode insertion tool 100 is manipulated in a proximal direction. The outer diameter of the dissecting portion 108 and/or proximally facing shoulder 114, in some embodiments, may be sized to be greater than the outer diameter of the lead assembly 102 such that, as the lead assembly 102 is pulled through subcutaneous tissue, drag on the lead assembly 102 is reduced to avoid damage during the pulling step. For example, the outer diameter of the dissecting portion 108 may be about 0.3 mm to about 5.0 mm larger than the outer diameter of a corresponding lead assembly 102 to reduce drag. In other embodiments, the outer diameter for the electrode insertion tool 100 is generally similar to the outer diameter of the lead assembly 102, which may reduce the level of patient discomfort during the procedure.

Figure 3B:
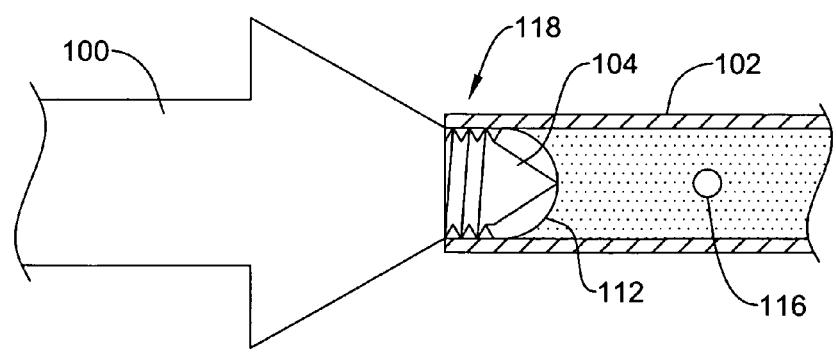

FIG. 3B is a side view of the electrode insertion tool and the lead of FIG. 3A in an attached configuration. As can be seen at 118, the electrode insertion tool 100 is secured to the lead assembly 102, with the cooperative threading of the engaging structures removably fixing the two pieces 100, 102 together. The cavity wall 112 is formed such that the dissecting tip 104 is easily received in the distal end of the lead assembly 102 while the electrode insertion tool 100 is attached to the lead assembly 102. Once the lead assembly 102 is drawn through a subcutaneous path and the distal end of the lead assembly 102 is at its desired location, the suture hole 116 may be used to secure the lead assembly in place. In the illustrative embodiment, the direct attachment of the lead assembly 102 to the electrode insertion tool 100 allows for a simple and quick implantation procedure.

Figure 4A:
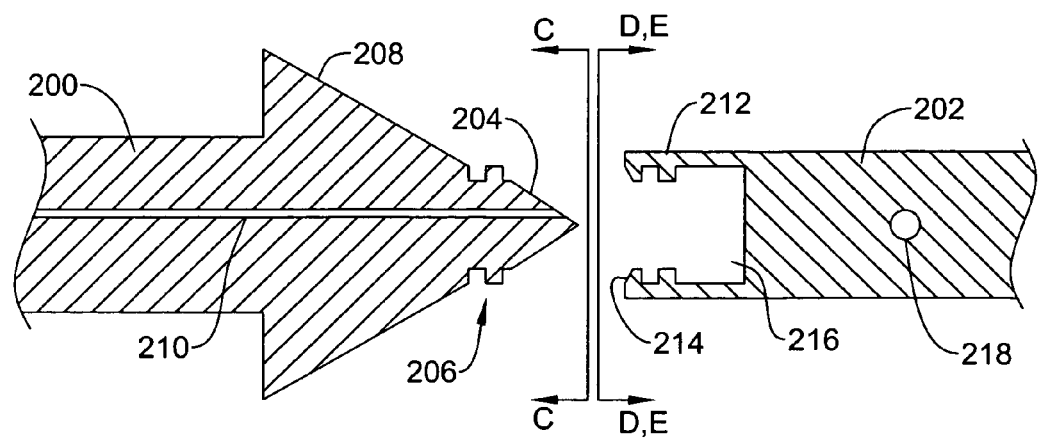
FIGS. 4A and 4B are longitudinal cross-sectional views of another illustrative electrode insertion tool and an illustrative lead in detached and attached configurations.

FIG. 4A is a longitudinal cross-sectional view of another illustrative electrode insertion tool 200 and an illustrative lead assembly 202 in a detached configuration. The electrode insertion tool 200 includes a dissecting tip 204, an engaging structure 206, and a dissecting portion 208. As before, the dissecting tip 204 may be sharp or blunt, and the dissecting portion 208 is sized to further expand a subcutaneous channel formed as the electrode insertion tool 200 is advanced through tissue.

In the embodiment of FIG. 4A, an internal channel 210 is also illustrated. The internal channel 210 may be used to infuse a fluid during the implantation procedure, for example, a local anesthetic, anti-inflammatory drugs, antibiotics, visualization media or any other suitable material, as desired. The channel 210 is shown with openings at various locations, including on the dissecting portion 208 as well as the more proximal shaft region of the electrode insertion tool 200. These openings may be placed as desired. In addition, an opening may be placed at or near the dissecting tip 204.

The embodiment of FIG. 4A also illustrates the illustrative lead assembly 202 as including an engaging structure 212, which generally includes a ridge 214, and a cavity 216. The cavity 216 and engaging structure 212 provide a receiving location for a distal portion of the electrode insertion tool 200 such that the ridge 214 secures the lead to the tool 200. The lead assembly 202 may also include a suture hole as shown at 218. As indicated by the alternate view lines, FIGS. 4C, 4D and 4E illustrate various forms for the engaging structures, and are further explained below. These structures may include select twist-locking structures and/or a slide-over or snap-fit structure, as further explained below.

Figure 4B:
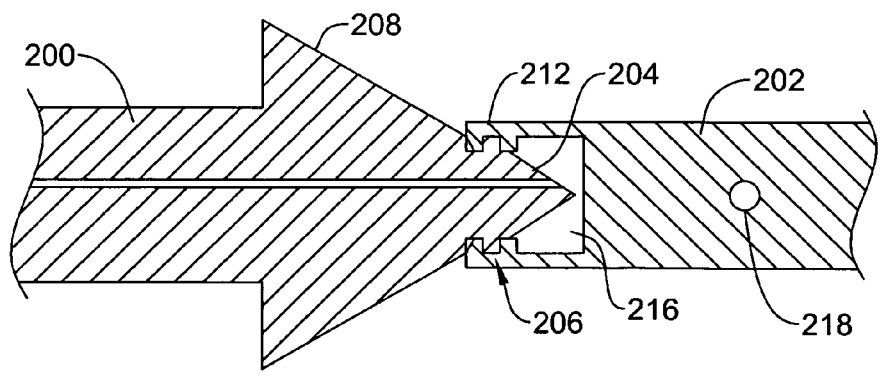
Figure 4C:
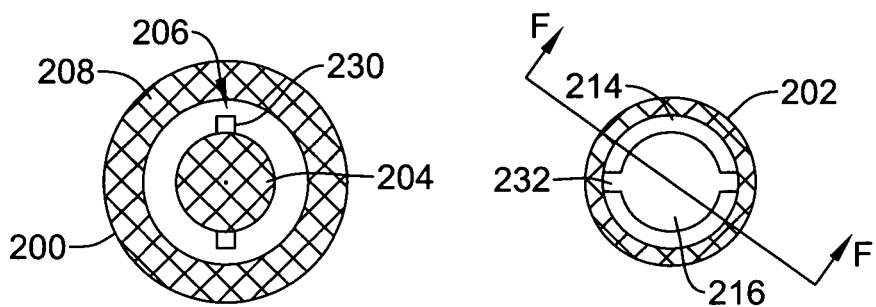
FIGS. 4C-4E are views of alternative constructions along lines C-C, D-D and E-E of the illustrative electrode insertion tool and illustrative lead of FIG. 4A.
Figure 4D:
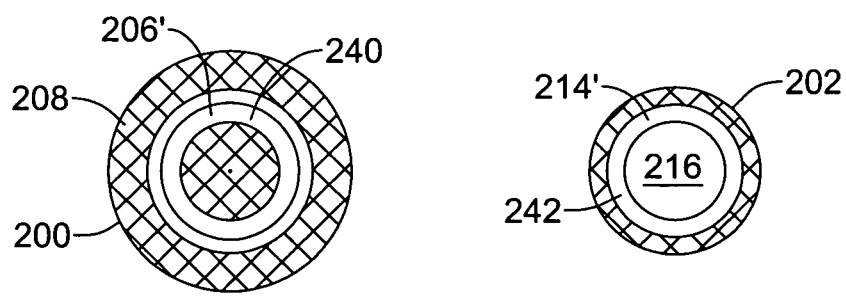
Figure 4E:
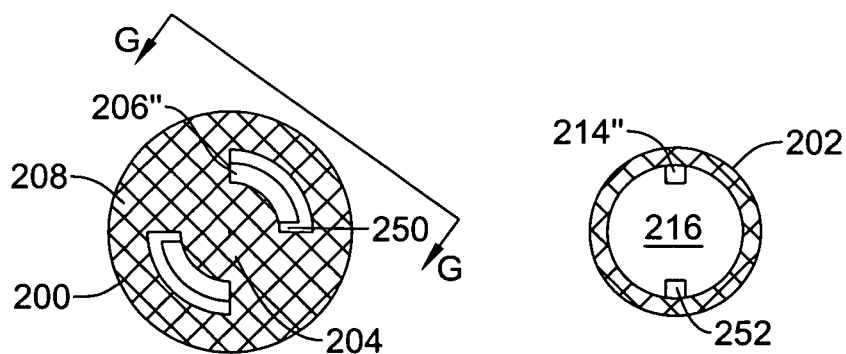

FIG. 4B is a longitudinal cross-sectional view of the electrode insertion tool and the illustrative lead of FIG. 4A in an attached configuration. When in the attached configuration, the dissecting tip 204 of the electrode insertion tool 200 is disposed in the cavity 216 of the lead assembly 202, with the tool engaging structure 212 of the lead assembly coupled to the lead engaging structure 206 of the electrode insertion tool 200.

Figure 4F:
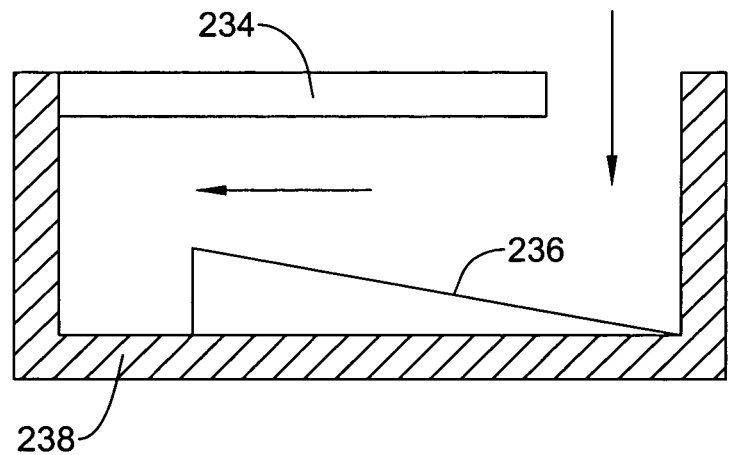
FIG. 4F is an illustrative cut-away view along line F-F of FIG. 4C.

FIGS. 4C-4E are elevation views of constructions along lines C-C, D-D and E-E of the illustrative electrode insertion tool 200 and illustrative lead assembly 202 of FIG. 4A. Referring to FIG. 4C, the electrode insertion tool 200 is shown as including the dissecting tip 204, lead engaging structure 206, and dissecting portion 208. The lead engaging structure 206 is shown generally at 230 as including a pair of tabs. The lead assembly 202 is shown as including a ridge 214 about cavity 216. The ridge 214 is shown generally as a disc that extends inward from an outer sheath into the chamber 216, the disc including a pair of gaps 232 that are spaced and sized to receive the tabs 230 of the lead engaging structure 206. Turning to FIG. 4F, it can be seen that the disc provides a ledge 234 for holding tabs 230. The tool engaging structure is shown in FIG. 4F as including a ramp 236 that leads up to a slot 238. When the tabs 230 are passed through the gaps 232 and the electrode insertion tool 200 is twisted relative to the lead assembly 202, at least one of the tabs passes over the ramp 236 until it crosses the end of the ramp 236 and settles into the slot 238. Maintaining even slight axial tension can help to hold the tabs 230 in the slot 238 as the electrode insertion tool is pulled from its proximal end.

Referring now to FIG. 4D, a slide-over or snap-fit structure is illustrated. In particular, the illustrative electrode insertion tool 200 includes an engaging structure 206' including an annular disc 240. The annular disc 240 projects out from the surface of the engaging structure, but with a lesser diameter than the outer diameter of the dissecting portion 208. The lead assembly 202 includes a chamber 216 and a ridge 214' which is also a disc 242 structure, this time projecting inward from the outer wall of the chamber 216. One, the other, or both of the discs 240, 242 may be flexible to allow the discs to be passed over one another.

Figure 4G:
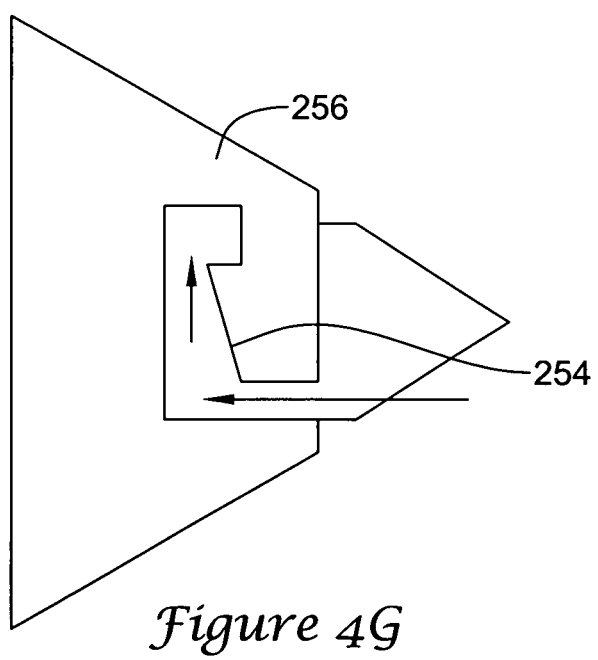
FIG. 4G is an illustrative view along line G-G of FIG. 4E.

Referring now to FIG. 4E, another construction is shown, this time with the electrode insertion tool 200 including an engagement structure 206" having a disc defining gaps 250. Again, the engagement structure 206" sits proximal of the dissecting tip 204 and distal of the dissecting portion 208. The lead assembly 202 includes a ridge 214" and a chamber 216, with the ridge 214" reduced to tabs 252 sized to fit through the gaps 250 of the electrode insertion tool 200. FIG. 4G shows the structure of the electrode insertion tool from line G-G. As can be seen, the engaging structure 206" on the electrode insertion tool 200 again includes the gap 250 and defines a channel for sliding the tabs 252 up a ramp 254 to a receiving slot 256. Again, a certain amount of axial tension may help to retain the tab(s) 252 in the slot 256.

In FIGS. 4C and 4E, the number and shape of the tabs 230, 252 may vary, and the particulars described in each structure are merely illustrative of some embodiments.

Figure 5A:
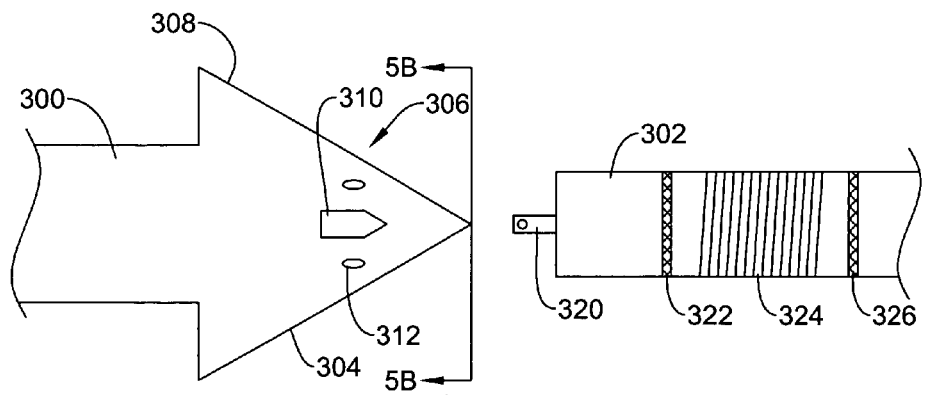
FIG. 5A is a side view of an illustrative electrode insertion tool and an illustrative lead in a detached configuration.

FIG. 5A is a side view of an illustrative electrode insertion tool 300 and an illustrative lead assembly 302 in a detached configuration. The electrode insertion tool 300 again includes a dissecting tip 304, an engaging structure 306, and a dissecting portion 308 which may be included to further dissect tissue. The engaging structure includes a slot 310 that is adapted to receive a corresponding engaging structure 320 on the lead assembly 302. Openings 312 are also shown and communicate with the slot 310, allowing a suture to pass therethrough.

The lead assembly 302 includes, as indicated, an engaging structure 320, which is shown as including a suture hole. The lead assembly 302, as with each lead assembly shown herein, may include any suitable number, configuration, and type of electrodes. One suitable configuration is shown in FIG. 5A as including a distal ring electrode 322 and a proximal ring electrode 326, with a coil electrode 324 therebetween. Other configurations may also be used, as suits the particular system, application, and patient. The lead assembly 302 includes an engaging structure 320 that extends therefrom. As explained below by reference to FIG. 5C, the engaging structure 320 of the lead assembly 302 is sized and shaped for placement in the slot 310 of the electrode insertion tool 300. Also, the engaging structure 320 of the lead assembly 302 is shown with a suture hole that may be used both in securing the lead assembly to the electrode insertion tool, and also for suturing to tissue after placement.

Figure 5B:
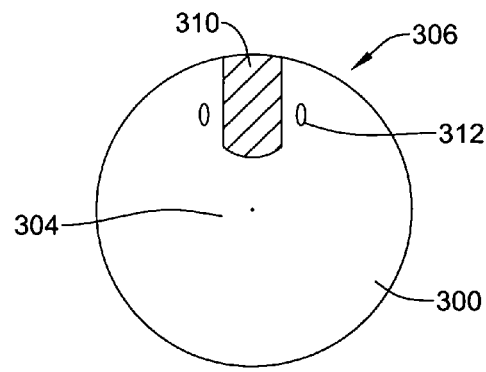
FIG. 5B is an axial elevation view of the distal end of the illustrative electrode insertion tool of FIG. 5A.

FIG. 5B is an axial elevation view of the distal end of the illustrative electrode insertion tool of FIG. 5A. The electrode insertion tool 300 includes the dissecting tip 304 and the engaging structure 306. The dissecting portion 308 is omitted, as it may be omitted in some embodiments not only of the electrode insertion tool 300 in FIGS. 5A-5C, but also in the other embodiments shown herein. The engaging structure 306 includes slot 310 and openings 312 that communicate with the slot 310.

Figure 5C:
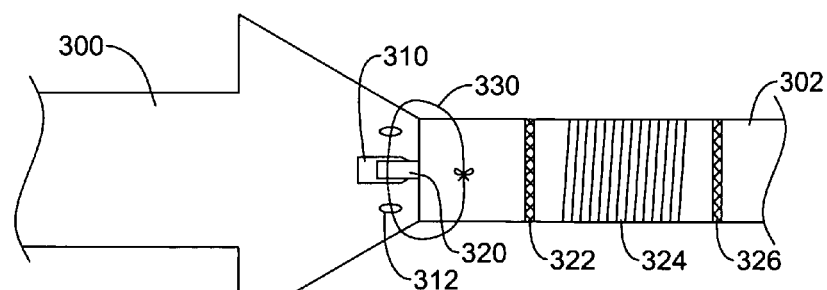
FIG. 5C is a side view of the illustrative electrode insertion tool and the illustrative lead of FIG. 5A in an attached configuration.

FIG. 5C is a side view of the illustrative electrode insertion tool and the illustrative lead of FIG. 5A in an attached configuration. As can be seen, the engaging structure 320 of the lead assembly 302 is inserted into the slot 310. A suture 330 passes through the openings 312 to the suture hole on the engaging structure 320 of the lead assembly 302 while it rests in the slot 310. As such, the suture 330 secures the lead assembly 302 to the electrode insertion tool 300. If desired, the engaging structure 320 of the lead assembly 302 may be shaped or marked to aid in correct alignment of the suture hole of the engaging structure 320 with the openings 312 and the slot 310. For example, the engaging structure 320 of the lead assembly may be oblong or polygonal.

In the embodiment of FIGS. 5A-5C, the electrode insertion tool 300 includes a receiving portion for receiving the engaging structure 320 of the lead assembly 302. The receiving portion includes the engaging structure 306 at the distal end of the electrode insertion tool.

FIG. 6A is a side view of an illustrative electrode insertion tool 400 and an illustrative lead assembly 402 in a detached configuration. The electrode insertion tool 400 includes a dissecting tip 404, an engaging structure 406 and a dissecting portion 416. The example lead assembly 402 includes an engaging structure 420 including a suture hole 422, as well as a configuration of multiple electrodes 424, 426, 428.

The illustrative engaging structure 406 includes a hook 408, elongate shaft 410, and actuator 412, with the actuator 412 shown as being associated with the device handle 414. The hook 408 is shown in a retracted position such that its distal end exits and then reenters the lead assembly 402. The actuator 412 is coupled to the elongate shaft 410 to control whether the hook 408 is in the retracted position shown in FIG. 6A or the extended position shown in FIG. 6B.

FIG. 6B is a side view of the illustrative electrode insertion tool and the illustrative lead of FIG. 6A in an attached configuration. The actuator 412 on the device handle 414 has been manipulated, such that the hook 408 extends from the distal end of the electrode insertion tool 400 and away from the reentry opening 418. The hook 408 has been placed into the suture hole 422 on the engaging structure 420 of the lead assembly 402. Thus, the engaging structure 406 of the electrode insertion tool 400 interacts with the engaging structure 420 of the lead assembly 402 to secure the two together. In some embodiments, a slot may be provided on the electrode insertion tool 400 to receive the engaging structure 420 of the lead assembly as well, for example, in a manner as shown in FIGS. 5A-5C.

Figure 7A:
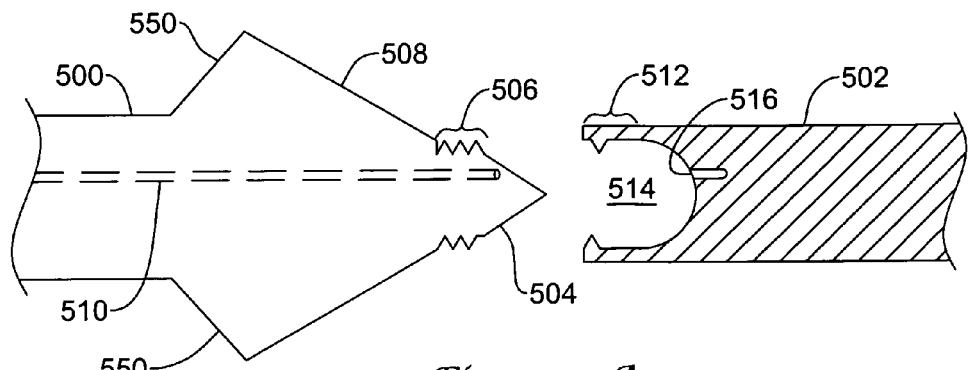
FIGS. 7A-7B are cross-sectional views of an illustrative electrode insertion tool and an illustrative lead assembly in detached and attached configurations to illustrate a locking mechanism.
Figure 7B:
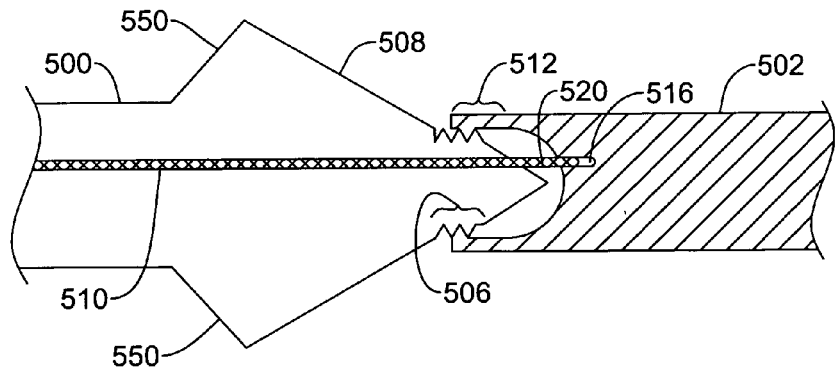
Figure 7C:
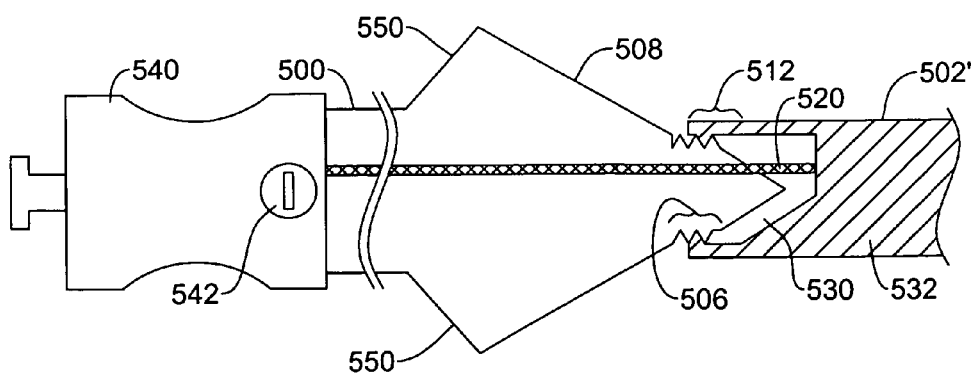
FIG. 7C illustrates another locking mechanism.

FIGS. 7A-7C show an illustrative embodiment in which a locking structure is provided in addition to the engaging structures. Referring to FIG. 7A, an electrode insertion tool 500 is shown detached from an illustrative lead assembly 502. The electrode insertion tool 500 includes a dissecting tip 504, and engaging structure 506 (shown as threading), and a dissecting portion 508. A locking structure 510 is also shown.

The lead assembly 502 includes an engaging structure 512 for threading onto the engaging structure 506 of the electrode insertion tool 500. The receiving chamber 514 is configured to receive the distal end of the electrode insertion tool 500. A locking structure 516 is also shown, and is further explained by reference to FIG. 7B.

Referring to FIG. 7B, the engaging structures 506, 512 of the electrode insertion tool 500 and lead assembly 502 are shown in a secured configuration. The locking structure 510 of the electrode insertion tool 500 is shown as including a locking key 520. When advanced as shown, the locking key 520 engages the locking structure 516 of the lead assembly 502, preventing the lead assembly 502 from becoming unthreaded from the electrode insertion tool 500.

FIG. 7C shows another embodiment, including the actuator 542 for the locking key 520. In particular, the actuator 542 may be part of the device handle 540. The locking key 520 may be coupled to the actuator 542 by an elongate shaft extending through the length of the electrode insertion tool 500. The embodiment of FIG. 7C shows an alternative to the locking structure 516 of FIGS. 7A-7B. In particular, rather than a small location that may receive the locking key 520, the lead assembly 502' may include a fin 532 that prevents full rotation of the lead assembly 502' relative to the electrode insertion tool 500 when the locking key 520 is disposed in the receiving chamber 530. Several fins 532 may be provided, or a solid member may be provided to take up a portion of the space in the receiving chamber 530 to prevent rotation of the lead assembly 502' relative to the electrode insertion tool 500.

FIGS. 7A-7C also illustrate an electrode insertion tool 500 which includes a distal enlargement for dissecting patient tissue that has a distally facing dissecting portion 508 as well as a proximally facing, non-abrupt shoulder 550. As discussed above, the proximally facing shoulder 550 may be formed to allow smooth passage through the already dissected subcutaneous tissue, while also creating a pathway for drawing the lead assembly 502, 502' easily therethrough. A smooth shoulder may be provided in any suitable fashion, for example, by smoothing the outer edge of the shoulder down, or by providing an angled shoulder, as is shown in FIGS. 7A-7C.

Figure 8A:
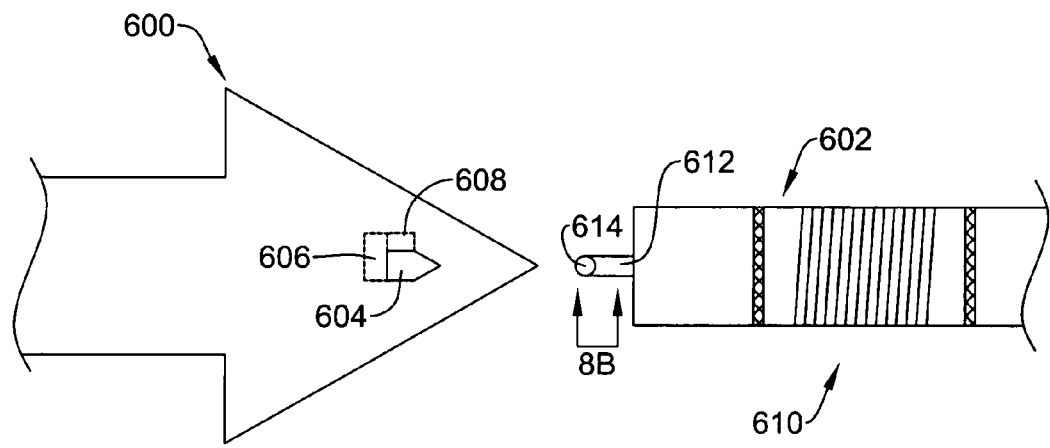
FIG. 8A is a side view of another illustrative electrode insertion tool and an illustrative lead in a detached configuration.

FIG. 8A is a side view of another illustrative electrode insertion tool 600 and an illustrative lead assembly 602 in a detached configuration. The electrode insertion tool 600 includes a receiving portion 604 located proximal of a dissecting tip, with an additional dissecting portion extending proximally of the receiving portion 604. The receiving portion 604 includes a channel 606 and a slot 608, with the channel 606 and the slot 608 shown in phantom to illustrate that they are not open to the outer surface of the electrode insertion tool 600. The illustrative lead assembly 602 includes electrodes 610 and an attachment structure 612 including a tab 614.

Figure 8B:
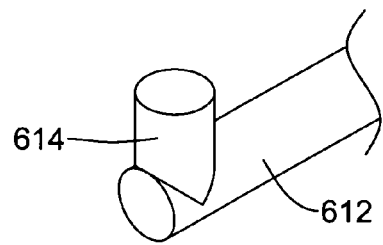
FIG. 8B is a closer view of the distal tip of the illustrative lead in FIG. 8A.

FIG. 8B is a closer view of the distal tip of the illustrative lead in FIG. 8A. The attachment structure 612 extends axially from the distal end of the lead assembly 602 (FIG. 8A). A tab 614 extends laterally from the distal end of the attachment structure 612. The attachment structure 612 and tab 614 are configured to cooperate with the receiving portion 604, channel 606 and slot 608 shown in FIG. 8A, as is further shown in FIGS. 8C-8D.

Figure 8C:
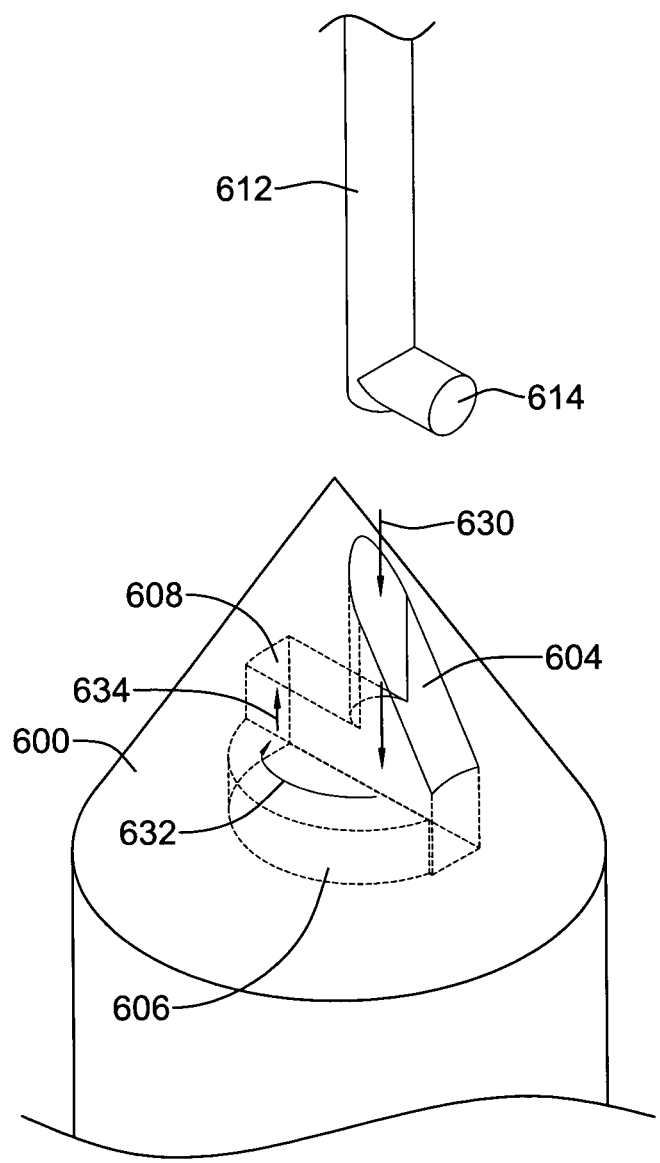
FIGS. 8C-8D are perspective views showing detached and attached configurations for the illustrative electrode insertion tool and illustrative lead of FIG. 8A.
Figure 8D:
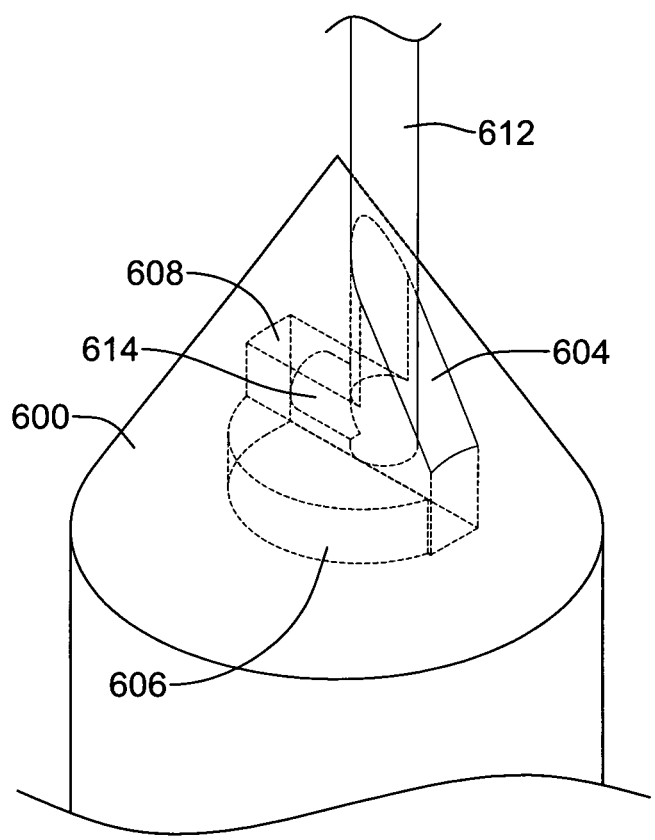

FIGS. 8C-8D are perspective views showing detached and attached configurations for the illustrative electrode insertion tool and illustrative lead of FIG. 8A. The attachment structure 612 is aligned such that the tab 614 aligns with the receiving portion 604. As indicated by arrow 630, the attachment structure 612 is inserted in the receiving portion 604 until the tab 614 is inside the receiving portion and aligns with the channel 606. As indicated by line 632, the attachment structure 612 and lead assembly are then rotated relative to the insertion tool 600 (or vice versa), such that the tab 614 slides through the channel 632.

In the illustrative embodiment of FIGS. 8A-8D, the slot 608 is included. The slot 608 is optional, and may be omitted if desired. As indicated by line 634, once the tab 614 slides through the channel 606 to a position in alignment with the slot 608, the lead assembly and insertion tool 600 are moved axially relative to one another such that the tab 614 enters the (optional) slot 608.

FIG. 8D shows the lead assembly secured to the insertion tool 600, with the attachment structure 812 engaged with the slot 608 after passing the tab 614 through the receiving portion 604 and channel 606. While in this configuration, the insertion tool 600 is drawn out through the subcutaneous path it established prior to being connected to the lead assembly. Once the insertion tool 600 has been withdrawn, the engaging structure 612 is disengaged by maneuvering the tab 614 out of the slot 608, into the channel 606, and around to the receiving structure 604.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A system for implanting an implantable cardiac stimulus device having an implantable canister, the system comprising:
    an introducer tool for implanting a lead for the implantable cardiac stimulus device, the introducer tool having a proximal end with a handle, a distal end including a dissecting tip, and a shaft therebetween, the distal end also including an engaging structure disposed on an outer portion of the shaft at a location proximal of but adjacent to the dissecting tip; and
    a cardiac electrode lead having at least one of a sensing electrode and/or a stimulus electrode disposed thereon, the lead comprising a first end having a receiving structure configured to receive the dissecting tip therein and engage the engaging structure of said introducer tool, and a second end having an attachment structure for attaching to the implantable canister; wherein:
    the engaging structure and the first end of the lead are configured for releasable coupling to one another;
    the engaging structure includes a threaded portion;
    the receiving structure includes threads for matching the engaging structure; and
    the threaded portion of the engaging structure forms part of an outer surface of the dissecting tip of the introducer tool.

2. The system of claim 1, wherein the receiving structure and the engaging structure are configured for twisting engagement thereof.

3. The system of claim 1, wherein the introducer tool further comprises means for locking the introducer tool and the cardiac electrode lead in an engaged state.

4. The system of claim 1 wherein the dissecting tip further comprises a dissecting portion proximal to the engaging structure, the dissecting portion shaped to further separate subcutaneous tissue relative to the dissecting tip such that, when the engaging structure is used to secure the lead thereto, and the handle is pulled in a proximal direction, the dissecting portion reduces drag on the lead.

5. The system of claim 4, wherein the dissecting tip, engaging structure, and dissecting portion of the tool generally form a conical portion with a discontinuity at the engaging structure, the discontinuity extending at least partly about the conical portion.

6. The system of claim 5, wherein the discontinuity extends wholly around the conical portion.

7. The system of claim 1, wherein the tool further comprises means for locking the tool to the lead when engaged therewith, and the lead further comprises corresponding means for locking the lead to the tool when engaged therewith.

8. The system of claim 1 wherein the tool further comprises a locking member coupled to a control mechanism disposed relative to the handle, the locking member configured to lock the tool in an engaged position in response to actuation by the control mechanism.

9. The system of claim 1 wherein the tool further includes a shoulder adjacent and proximal to the dissecting tip, wherein the shoulder is shaped for non-traumatic passage in a proximal direction through subcutaneous tissue such that atraumatic passage of the lead occurs when the tool is withdrawn through tissue while engaged with the lead at the engaging structure of the tool.

* * * * *